United States Patent
Arntz et al.

(10) Patent No.: US 10,633,330 B2
(45) Date of Patent: Apr. 28, 2020

(54) PROCESS FOR PREPARING LIQUID, STORAGE-STABLE ORGANIC ISOCYANATES HAVING CARBODIIMIDE AND/OR URETONIMINE GROUPS AND HAVING LOW COLOUR NUMBER

(71) Applicant: Covestro Deutschland AG, Leverkusen (DE)

(72) Inventors: Hans-Detlef Arntz, Overath (DE); Torsten Hagen, Essen (DE); Ernst Felske, Neuss (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 16/328,748

(22) PCT Filed: Sep. 7, 2017

(86) PCT No.: PCT/EP2017/072517
§ 371 (c)(1),
(2) Date: Feb. 27, 2019

(87) PCT Pub. No.: WO2018/046622
PCT Pub. Date: Mar. 15, 2018

(65) Prior Publication Data
US 2019/0202777 A1    Jul. 4, 2019

(30) Foreign Application Priority Data
Sep. 8, 2016 (EP) ..................... 16187725

(51) Int. Cl.
| | | |
|---|---|---|
| *C07C 263/16* | (2006.01) | |
| *C07C 267/00* | (2006.01) | |
| *C08G 18/80* | (2006.01) | |
| *C08G 18/32* | (2006.01) | |
| *C08G 18/79* | (2006.01) | |
| *C07C 263/18* | (2006.01) | |

(52) U.S. Cl.
CPC .......... *C07C 263/16* (2013.01); *C07C 263/18* (2013.01); *C07C 267/00* (2013.01); *C08G 18/3206* (2013.01); *C08G 18/797* (2013.01); *C08G 18/8019* (2013.01)

(58) Field of Classification Search
CPC ... C07C 263/16; C07C 265/14; C07C 263/18; C07C 267/00; C08G 18/3206; C08G 18/797; C08G 18/8019
See application file for complete search history.

(56) References Cited

U.S. PATENT DOCUMENTS

| | | | |
|---|---|---|---|
| 2,853,473 A | 9/1958 | Campbell | |
| 4,088,665 A | 5/1978 | Findeisen et al. | |
| 4,218,543 A | 8/1980 | Weber et al. | |
| 5,202,358 A * | 4/1993 | Scholl | C07C 267/00 252/182.2 |
| 5,354,888 A | 10/1994 | Scholl | |
| 6,120,699 A | 9/2000 | Narayan et al. | |
| 7,030,274 B2 | 4/2006 | Rosthauser et al. | |
| 7,825,276 B2 | 11/2010 | Wershofen et al. | |
| 8,022,200 B2 | 9/2011 | Wershofen et al. | |
| 2006/0128928 A1 | 6/2006 | Wershofen et al. | |
| 2007/0213496 A1 | 9/2007 | Savino et al. | |

FOREIGN PATENT DOCUMENTS

| | | | |
|---|---|---|---|
| DE | 2537685 A1 | | 3/1977 |
| EP | 0515933 | * | 12/1992 |
| EP | 0515933 A2 | | 12/1992 |
| EP | 1671988 A2 | | 6/2006 |

OTHER PUBLICATIONS

Z. Pakulski, R. Kwiatosz and K. M. Pietrusiewicz, "Cyclopentannulation on 3-phospholenes: an expedient route to the 2-phosphabicyclo[3.3.0]octene ring system", Tetrahedron Letters 44 (2003), 5469-5472.

* cited by examiner

*Primary Examiner* — Yevgeny Valenrod
*Assistant Examiner* — Blaine G Doletski
(74) *Attorney, Agent, or Firm* — Donald R. Palladino

(57) ABSTRACT

The invention relates to a process for preparing liquid, storage-stable isocyanate mixtures having carbodiimide (CD) and/or uretonimine (UI) groups or prepolymers derived therefrom, wherein (i) in a first step, a starting isocyanate which is an organic isocyanate or a mixture of two or more organic isocyanates is partly carbodiimidized with a catalyst K of the formula cyclo-$C_4H_6P(O)R$, where the substituent R is a saturated or unsaturated, optionally substituted, especially halogen-substituted, organic radical, and then (ii) in a second step, the carbodiimidization reaction is stopped at a temperature of ≤80° C. by adding a stopper, the stopper used being an organic silane S of the general formula $H_nSiX_{4-n}$, where n is a natural number in the range from 1 to 3, where X is a saturated or unsaturated, optionally substituted, especially halogen-substituted, organic radical.

15 Claims, No Drawings

PROCESS FOR PREPARING LIQUID, STORAGE-STABLE ORGANIC ISOCYANATES HAVING CARBODIIMIDE AND/OR URETONIMINE GROUPS AND HAVING LOW COLOUR NUMBER

CROSS-REFERENCE TO RELATED APPLICATIONS

This application is a national stage application under 35 U.S.C. § 371 PCT/EP2017/072517, filed Sep. 7, 2017, which claims the benefit of European Application No. 16187725.3, filed Sep. 8, 2016, both of which being incorporated by reference herein.

FIELD

The invention relates to a process for preparing liquid, storage-stable isocyanate mixtures having carbodiimide (CD) and/or uretonimine (UI) groups and prepolymers derived therefrom, wherein
(i) in a first step, a starting isocyanate which is an organic isocyanate or a mixture of a plurality of organic isocyanates is partially carbodiimidized using a catalyst K of the formula cyclo-$C_4H_6P(O)R$, where the substituent R is a saturated or unsaturated, optionally substituted, in particular halogen-substituted, organic radical, and subsequently
(ii) in a second step, the carbodiimidization reaction is stopped at a temperature of ≤80° C. by addition of a stopper,
where an organic silane S of the general formula $H_nSiX_{4-n}$, where X is a saturated or unsaturated, optionally substituted, in particular halogen-substituted, organic radical, is used as stopper.

BACKGROUND

Isocyanate mixtures having CD and/or UI groups can be prepared in a simple manner using the highly active catalysts of the phospholine series, in particular the phospholine oxide series, by the processes as described in U.S. Pat. Nos. 2,853,473, 6,120,699 and EP-A-0 515 933.

The high catalytic activity of the phospholine catalysts, in particular the phospholine oxide catalysts, is desirable on one hand in order to promote the carbodiimidization reaction under mild temperature conditions, but on the other hand the effective stopping of the phospholine catalysis or the phospholine oxide catalysis has up to now not been without challenges. The carbodiimidized isocyanates tend to undergo an after-reaction, i.e. they outgas as a result of $CO_2$ evolution. This then leads, particularly at relatively high temperatures, to a buildup of pressure, for example in the storage vessels. In addition, obtaining light-colored products and in particular the color stability after prolonged storage can be problematic time and again.

There have been many attempts to find an effective way of stopping the phospholine catalysis. Such stoppers are, for example, mentioned in the patent applications DE-A-25 37 685, EP-A-0 515 933, EP-A-0 609 698, EP-A-1 607 425, U.S. Pat. No. 6,120,699 and US 2007/213496 and comprise, for example, acids, acid chlorides, chloroformates, silylated acids and halides of the main group elements. Stoppers disclosed in the prior art are, in particular, ethyl trifluoromethylsulfonate (ETF), trimethylsilyl trifluoromethanesulfonate (TMST) as methylating or silylating reagent or strong acids such as trifluoromethanesulfonic acid (TFMSA) or perchloric acid.

According to the teaching of EP-A-0 515 933, CD/UI-containing isocyanate mixtures prepared by means of phospholine catalysis are stopped using at least the equimolar amount, preferably the 1- to 2-fold molar amount, based on the catalyst used, of a silylated acid (or ester thereof), for example trimethylsilyl trifluormethanesulfonate (TMST). However, it has been found in practice that CD/UI-containing isocyanates prepared in this way have only limited suitability for the preparation of prepolymers, i.e. reaction products of these CD/UI-containing isocyanates with polyols. The reaction products prepared in this way from polyols and the CD/UI-modified isocyanates tend to outgas, which can lead to a buildup of pressure in the transport containers or to foaming when handling such products.

This problem can be circumvented by using the silylated acid employed for stopping the phospholine catalyst in a manner analogous to EP-A-0 515 933 in higher molar equivalents (e.g. from 5:1 to 10:1, based on the catalyst). However, it is found in practice that the CD/UI-modified isocyanates obtained then have a significantly poorer color number. This then also applies to the prepolymers prepared therefrom.

This also applies when the phospholine catalyst is stopped using acids of the trifluoromethanesulfonic acid type as per U.S. Pat. No. 6,120,699. Prepolymers prepared therefrom also have a considerably increased color number.

According to the teaching of EP-A-1 616 858, an unsilylated acid and/or an acid chloride and/or sulfonic ester is used in addition to the silylated acid described in EP-A-0 515 933. However, this is also not able to solve the indicated problems completely since the catalyst can become less active when subjected to temperature stress during storage or during further processing to give (semi)prepolymers.

According to the teaching of EP-A-1 671 988, an alkylating agent, preferably an ester of trifluoromethanesulfonic acid, is used as stopper. However, this method has the disadvantage that the condensation reaction can start again on addition of polyols as are used in the preparation of prepolymers, which leads to lower than expected isocyanate contents.

WO 2007/076998 teaches carrying out the carbodiimidization in the presence of a secondary or tertiary amine and stopping the reaction by means of the known reagents of the prior art. These additives serve to bind the hydrochloric acid which is present in traces in the isocyanate as a result of the method of production and impairs carbodiimide formation, and only indirectly increase the stability of the product because the catalyst concentration can be reduced only slightly without increasing the reaction times.

US 2007/213496 discloses the preparation of carbodiimide-containing polyisocyanates in the presence of phospholine oxide derivatives as catalysts at moderate reaction temperatures of from 80° C. to 130° C. Stopping of the reaction is carried out in two stages with gradually decreasing temperature. In the first stage, an acid, a peroxide or acid chloride is preferably used as stopper.

It is common to all the processes described in the prior art that the stability of the resulting carbodiimide-containing polyisocyanates during prolonged storage and/or under temperature stress and/or in the case of a pH change (the latter two aspects are particularly important for further processing to form prepolymers) is frequently unsatisfactory. This can result in worsening of color and renewed commencement of the condensation reaction to the carbodiimide which proceeds with elimination of $CO_2$. Even without prolonged storage, the color of carbodiimide-containing polyisocyanates is not always satisfactory.

Further improvements in this field of technology would therefore be desirable. In particular, it would be desirable to have available a process for preparing liquid isocyanate mixtures having carbodiimide and/or uretonimine groups, which does not have the abovementioned defects. The liquid isocyanate mixtures having carbodiimide and/or uretonimine groups to be prepared should, in particular, have low color numbers and be storage-stable, i.e. the color value, NCO content and viscosity should change very little during storage. In particular, it would also be desirable for the liquid isocyanate mixtures having carbodiimide and/or uretonimine groups prepared in this way to be able to be converted into prepolymers having a low color number and high storage stability.

SUMMARY

Taking into account what has been said above, the invention provides a process for preparing organic isocyanates having carbodiimide and/or uretonimine groups, wherein
(i) in a first step, a starting isocyanate which is an organic isocyanate or a mixture of a plurality of organic isocyanates is partially carbodiimidized using a catalyst K of the phospholine oxide type and subsequently
(ii) in a second step, the carbodiimidization reaction is stopped at a temperature of ≤80° C. by addition of a stopper,
where an organic silane S of the general formula $H_nSiX_{4-n}$, where n is a natural number in the range from 1 to 3 and X is a saturated or unsaturated, optionally substituted, in particular halogen-substituted, organic radical, in particular methyl or phenyl, particularly preferably phenyl ($C_6H_5$), is used as stopper. Particular preference is given to: X=phenyl and n=2 or 3.

A brief summary of various possible embodiments of the invention will firstly be given below:

In a first embodiment of the invention, which can be combined with all other embodiments, an isocyanate having an APHA Hazen color number of ≤100, preferably ≤50, is used as starting isocyanate.

In a second embodiment of the invention, which can be combined with all other embodiments as long as these do not provide for the use of starting isocyanates other than the following, the starting isocyanate is selected from the group consisting of
  tolylene disocyanate (TDI) and
  methylenedi(phenyl isocyanate) as isomer mixture in any proportions of the 2,2', 2,4' and 4,4' isomers.

In a third embodiment of the invention, which can be combined with all other embodiments as long as these do not provide for the use of starting isocyanates other than the following, the starting isocyanate is selected from the group consisting of
  4,4'-methylenedi(phenyl isocyanate) containing up to 4.0% by mass of 2,2'-methylenedi(phenyl isocyanate), based on the total mass of all methylenedi(phenyl isocyanate) isomers and
  mixtures of 2,4'-methylenedi(phenyl isocyanate) and 4,4'-methylenedi(phenyl isocyanate) containing up to 4.0% by mass of 2,2'-methylenedi(phenyl isocyanate), based on the total mass of all methylenedi(phenyl isocyanate) isomers.

In a fourth embodiment of the invention, which can be combined with all other embodiments as long as these do not provide for the use of starting isocyanates other than that defined below, the starting isocyanate contains at least 99.0% by mass, preferably 99.5% by mass, based on the total mass of the starting isocyanate, of methylenedi(phenyl isocyanate) isomers, where the proportion of 4,4'-methylenedi(phenyl isocyanate), based on the totality of all methylenedi(phenyl isocyanate) isomers in the starting isocyanate, is at least 97.0%, preferably at least 98.0%.

In a fifth embodiment of the invention, which can be combined with all other embodiments as long as these do not provide for the use of starting isocyanates other than that defined below, a mixture of methylenedi(phenyl isocyanate) isomers and polymethylenepolyphenylene polyisocyanate having a total content of methylenedi(phenyl isocyanate) isomers of from 15% by mass to <95% by mass, based on the total mass of methylenedi(phenyl isocyanate) isomers and polymethylenepolyphenylene polyisocyanate, is used as starting isocyanate.

In a sixth embodiment of the invention, which can be combined with all other embodiments:
  X=phenyl and n=2 or 3.

In a seventh embodiment of the invention, which can be combined with all other embodiments, one of the following compounds or a mixture of the two:

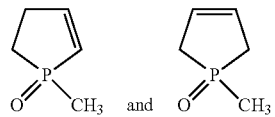

is used as catalyst K of the phospholine oxide type.

In an eighth embodiment of the invention, which can be combined with all other embodiments, the carbodiimidization reaction in step (i) is carried out in the temperature range from 50° C. to 150° C., preferably from 60° C. to 100° C.

In a ninth embodiment of the invention, which can be combined with all other embodiments, the carbodiimidization reaction of step (i) is stopped according to step (ii) on reaching a degree of carbodiimidization in the range from 3.0% to 50%.

In a tenth embodiment of the invention, which can be combined with all other embodiments, a molar ratio n(S)/n(K) of organic silane S to catalyst K in the range from 1 to 20 is used.

In an eleventh embodiment of the invention, which can be combined with all other embodiments, the reaction mixture of step (i) is cooled to a temperature in the range from 50° C. to 70° C. before carrying out step (ii).

In a twelfth embodiment of the invention, which can be combined with all other embodiments apart from the thirteenth embodiment described below, no further stopper is used in addition to the silane S in step (ii).

In a thirteenth embodiment of the invention, which can be combined with all other embodiments apart from the twelfth embodiment, a further stopper selected from the group consisting of acids, acid chlorides, sulfonic esters and mixtures of the abovementioned substances is used in addition to the silane S in step (ii).

In a fourteenth embodiment of the invention, which can be combined with all other embodiments, the organic isocyanate having carbodiimide and/or uretonimine groups which is obtained in step (ii) is reacted with a polyol to give a prepolymer.

DETAILED DESCRIPTION

The embodiments which have been indicated briefly above and further possible embodiments of the invention are explained in more detail below. Different embodiments can, unless the contrary is apparent to a person skilled in the art from the context, be combined with one another in any way.

As starting isocyanates for the process of the invention, it is possible to use any organic isocyanates, in particular those having an APHA Hazen color number (platinum-cobalt color number) of ≤100, preferably ≤50. The standard for determining the Hazen color number is the method DIN EN ISO 6271-1:2005-03 in bulk against an aqueous hydrochloric acid solution of potassium hexachloroplatinate(IV)/cobalt(II) chloride as reference at a path length of 5 cm. As measuring instrument, it is possible to use, for example, an LICO® 100 photometer from the company Dr. Lange.

The process of the invention is preferably used for the carbodiimidization of organic diisocyanates and polyisocyanates which are, in particular, used in polyurethane chemistry. Suitable examples are in particular:

aromatic diisocyanates such as (i) tolylene diisocyanate (TDI), in particular mixtures of 2,4- and 2,6-TDI ("meta-TDI"), (ii) methylenedi(phenyl isocyanate) as isomer mixture in any proportions of the 2,2', 2,4' and 4,4' isomers, in particular 4,4'-methylenedi(phenyl isocyanate) and also mixtures of 2,4'-methylenedi(phenyl isocyanate) and 4,4'-methylenedi(phenyl isocyanate), with in each case up to 4.0% by mass of the 2,2' isomer, based on the respective total mass of methylenedi (phenyl isocyanate) isomers, being able to be present in the latter two groups of substances;

mixtures of methylenedi(phenyl isocyanate) isomers and polymethylenepolyphenylene polyisocyanate having a total content of methylenedi(phenyl isocyanate) isomers of from 15% by mass to <95% by mass, based on the total mass of methylenedi(phenyl isocyanate) isomers and polymethylenepolyphenylene polyisocyanate.

The starting isocyanate particularly preferably contains at least 99.0% by mass, preferably 99.5% by mass, based on the total mass of the starting isocyanate, of methylenedi (phenyl isocyanate) isomers, where the proportion of 4,4'-methylenedi(phenyl isocyanate), based on the totality of all methylenedi(phenyl isocyanate) isomers in the starting isocyanate, is at least 97.0%, preferably at least 98.0% (owing to the identical molar mass of the various methylenedi (phenyl isocyanate) isomers, it is immaterial whether % by mass or mol % is used as basis).

The preparation of such organic isocyanates is adequately known in the prior art and will therefore not be described in more detail at this point.

Step (i) of the process of the invention is carried out in the presence of catalysts K of the phospholine oxide type. For the purposes of the present invention, catalysts of the phospholine oxide type are 1-oxophosphacyclopentenes, cyclo-$C_4H_6P(O)R$, which are substituted on the phosphorus atom, where the substituent R is a saturated or unsaturated, optionally substituted, in particular halogen-substituted, organic radical, in particular methyl or phenyl. The catalysts of the phospholine oxide type are known, for example, from EP-A-0 515 933 and U.S. Pat. No. 6,120,699. Typical examples of these catalysts are, in particular, the mixtures of the phospholine oxides of the formulae:

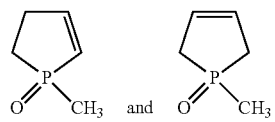

which are known from the prior art.

The amount of catalyst used depends on the quality of the starting isocyanates. The required amount of catalyst can therefore in each case be determined most simply in a preliminary test.

The carbodiimidization reaction in step (i) is preferably carried out in the temperature range from 50° C. to 150° C., more preferably from 60° C. to 100° C. The optimum reaction temperature depends on the type of starting isocyanates and/or the catalyst used and can be determined in a simple preliminary test.

The carbodiimidization reaction is preferably stopped on reaching a degree of carbodiimidization of from 3.0% to 50%, preferably from 5.0% to 30%. Here, the degree of carbodiimidization is the percentage of carbodiimidized isocyanate groups based on the total amount of the isocyanate groups present in the starting isocyanate. The degree of carbodiimidization can be determined while carrying out the process of the invention by determining the isocyanate content, e.g. by means of the titration as is known per se to a person skilled in the art (EN ISO 11909:2007, appendix A) or by means of on-line methods. One suitable on-line method is, for example, near infrared or middle infrared analysis. The degree of carbodiimidization can likewise be recognized while carrying out the process of the invention from, for example, the amount of carbon dioxide condensation product given off from the reaction mixture (1 mol of $CO_2$ is formed in the condensation of 2 mol of NCO groups). This amount of carbon dioxide, which can be determined volumetrically by means of a gas meter, thus gives information about the degree of carbodiimidization attained at any point in time. Furthermore, it is in principle also possible to use other suitable off-line or on-line methods of monitoring the process which are known to a person skilled in the art. All of these measurement methods basically give the same results within usual ranges of error which are insignificant for the purposes of the invention. Should, contrary to expectations, this not be the case in a particular instance, the degree of carbodiimidization determined from the amount of carbon dioxide given off as determined by volumetric measurement (as described above) and the isocyanate content of the starting isocyanate determined by titration in accordance with EN ISO 11909:2007 is decisive. In the experiments described in the examples, the volume flow of the condensation product $CO_2$ was monitored continuously by means of a gas meter (referred to as a "gas clock").

To end the carbodiimidization reaction in step (ii), an organic silane of the general formula $H_nSiX_{4-n}$, where n is a natural number in the range from 1 to 3, X is a saturated or unsaturated, optionally substituted, in particular halogen-substituted, organic radical, in particular methyl or phenyl, particularly preferably phenyl ($C_6H_5$), is used as stopper. It is also possible to use a mixture of various silanes of the type mentioned. The additional use of other stoppers is not necessary and is therefore also not carried out in a preferred embodiment of the invention. Particular preference is given to X=$C_6H_5$ and, due to the lower melting point (and the associated easier processability) of monophenylsilane or diphenylsilane compared to triphenylsilane, n=2 or 3, in particular n=2.

Organic silanes which can be used according to the invention are commercially available. The use of phenylsilane in the synthesis of 2-phosphabicyclo[3.3.0]octane ring systems is described in *Tetrahedron Letters* 44 (2003), 5469-5472 (authors: Z. Pakulski, R. Kwiatosz and K. M. Pietrusiewicz).

The organic silane is preferably used in an at least equimolar amount based on the molar amount of the catalyst of the phospholine oxide type used. In particular, preference is given to using an up to 20-fold, particularly preferably up to 10-fold, molar excess of the organic silane, based on the molar amount of the catalyst of the phospholine oxide type used.

Before the addition of the organic silane, the reaction mixture containing the organic isocyanate having carbodiimide and/or uretonimine groups which is obtained in step (i) is, if necessary, cooled to a temperature of ≤80° C., preferably to a temperature in the range from 50° C. to 70° C. Should the reaction in step (i) be carried out at a temperature of ≤80° C., in particular at a temperature in the range from 50° C. to 70° C., further cooling is superfluous and the stopper is added immediately after step (i).

As an alternative to the sole use of silanes as stoppers, it is possible to use, in another preferred embodiment of the process of the invention, a combination of a silane with an acid and/or an acid chloride and/or a sulfonic ester as additional stabilizer (which likewise acts as stopper). The amount of silane used can be reduced by the concomitant use of an additional stabilizer. The addition of this stabilizer can be carried out either simultaneously with the addition of the stopper or in a subsequent step.

As acids, it is possible to use optionally halogenated, aliphatic and/or cycloaliphatic and/or aromatic monocarboxylic, dicarboxylic and/or polycarboxylic acids such as acetic acid, adipic acid, cyclohexanedicarboxylic acid, α-chloropropionic acid, benzoic acid, phthalic acid, isophthalic acid, etc., and also sulfonic acids, HCl, sulfuric acid and/or phosphoric acid or monoesters and/or diesters thereof, e.g. dibutyl phosphate. As acid chlorides, it is possible to use the acid chlorides and also carbamoyl chlorides derived from the optionally halogenated, aliphatic and/or cycloaliphatic and/or aromatic monocarboxylic, dicarboxylic and/or polycarboxylic acids or sulfonic acids, e.g. n-butylcarbamoyl chloride. As sulfonic esters, it is possible to use, for example, methyl p-toluenesulfonate, ethyl p-toluenesulfonate.

The additional stabilizers are added in total amounts in the range from 10 ppm to 1000 ppm (1 ppm: 1 part by mass per 1 000 000 parts by mass), preferably from 10 ppm to 500 ppm, particularly preferably from 50 ppm to 250 ppm, based on the mass of the starting isocyanate.

The use of color stabilizers as are usually added to isocyanates is also possible in the process of the invention. The color stabilizers can preferably be added to the reaction product after the reaction is complete. Such stabilizers are generally known to those skilled in the art and encompass, for example, substances from the group consisting of sterically hindered phenols, phosphorous esters and tertiary amines. The color stabilizers can each be used alone or in admixture with other representatives of the same or different groups of substances. The amounts of the color stabilizers used vary in the range known to a person skilled in the art, usually in the range from 100 ppm to 10 000 ppm for the individual substance or the mixture, based on the isocyanate used as starting material or the reaction product of the carbodiimidization.

It has been found that the addition of the organic silanes either alone or in combination with an acid and/or an acid chloride and/or a sulfonic ester as additional stabilizer in the process of the invention enables the phospholine oxide catalysis to be effectively stopped and at the same time allows low color values in the resulting carbodiimide-modified isocyanate and prepolymers prepared therefrom to be obtained. When silylated acid is used as stopper as per the prior art (EP-A-0 515 933), the phospholine oxide catalysis can be effectively stopped only by addition of large amounts of silylated acid, but this leads to increased color values of the isocyanate mixtures produced in this way and prepolymers prepared therefrom.

Prepolymers containing isocyanate groups are obtained by reaction of the organic isocyanates having carbodiimide and/or uretonimine groups which have been prepared by the process of the invention with polyols customary in polyurethane chemistry. Suitable polyols are firstly simple polyhydric alcohols having a molecular mass in the range from 62 g/mol to 599 g/mol, preferably from 62 g/mol to 300 g/mol, in particular ethylene glycol, trimethylolpropane, 1,2-propanediol, 1,2-butanediol, 2,3-butanediol, 1,3-butanediol, 1,4-butanediol, hexanediol, octanediol, dodecanediol and/or octadecanediol. Among the group of simple polyhydric alcohols, particular preference is given to 1,2-propanediol, 1,3-butanediol, 1,4-butanediol or mixtures of these alcohols.

Suitable (and more preferred) polyols are, on the other hand, relatively high molecular weight polyether polyols and/or polyester polyols of the type known per se from polyurethane chemistry which have number average molar masses of from 600 g/mol to 8000 g/mol, preferably from 800 g/mol to 4000 g/mol, and have at least two, in particular from 2 to 8, preferably from 2 to 4, primary and/or secondary hydroxyl groups. Examples of such polyols are described in the U.S. Pat. No. 4,218,543, column 7, line 29 to column 9, line 32.

The advantages of the process of the invention are obvious: both the isocyanates containing carbodiimide and/or uretonimine groups and the prepolymers prepared therefrom have good storage stability and a light color.

These organic isocyanates having carbodiimide and/or uretonimine groups and the prepolymers prepared therefrom by reaction with polyols are valuable starting materials for producing synthetic polyurethane foams by reaction with polyols (e.g. with polyether polyols or polyester polyols) by the isocyanate polyaddition process.

EXAMPLES

Starting Materials:
Isocyanate: Desmodur 44M®, Covestro Deutschland AG (4,4'-methylenedi(phenyl isocyanate), NCO content: 33.6% by mass);
Catalyst: phospholine oxide type: industrial mixture of 1-methyl-1-oxo-1-phosphacyclopent-2-ene and 1-methyl-1-oxo-1-phosphacyclopent-3-ene in toluene (proportion by mass 1.0%);
Antioxidant: octadecyl 3-(3,5-di-tert-butyl-4-hydroxyphenyl)propionate (Irganox 1076 Ciba®);
Stopper: ethyl trifluoromethanesulfonate (ETFMS), phenylsilane, diphenylsilane, triphenylsilane (all from Aldrich) or Baysilon MH15 ("Momentive", Covestro Deutschland AG, polymethylhydrogensiloxane),
Polyol: linear propylene glycol-initiated propylene oxide polyether having a hydroxyl number of 515 mg KOH/g and a viscosity of 55 mPas at 23° C.

Analytical Methods:
Isocyanate content: EN ISO 11909:2007, appendix A;
Viscosity: DIN 53019-1:2008-09; rotational viscometer from Anton Paar;
Hazen color number (=APHA Hazen color number, platinum-cobalt color number): DIN EN ISO 6271-1:2005-03.

I. General Method for Preparing the Organic Isocyanate Having Carbodiimide and/or Uretonimine Groups and for Carrying Out Storage Tests:

1. 1000 kg of Desmodur 44M® having a Hazen color number of <15 APHA are heated to 90° C. in a nitrogen atmosphere while stirring. The amount indicated in table 1 of catalyst is subsequently added as 0.1% strength solution in toluene. The reaction mixture is heated at 95° C. in a nitrogen atmosphere while stirring until the NCO content indicated in the following table has been reached. The stopper is added to the reaction mixture at the temperature indicated in the table. The mixture is then stirred further at 100° C. for from 1 to 1½ hours. The NCO content indicated is determined 24 hours after the reaction is complete (A experiments).
2. A partial amount of the carbodiimide-modified isocyanates obtained in this way is stored in a tightly closed aluminum bottle for three days at 100° C. in a drying oven to assess its storage stability, before NCO content and viscosity are determined again (B experiments).

TABLE 1

Preparation of CD/UI-modified isocyanates (A experiments) and storage tests (B experiments)

|  | Unit | Example A1 (comparison) | Example A2 (according to the invention) |
|---|---|---|---|
| Desmodur 44M ® | [g] | 1000 | 1000 |
| Catalyst | [g] | 0.00400 | 0.00427 |
| ETFMS | [g] | 0.050 | 0 |
| Diphenylsilane | [g] | 0 | 0.1554 |
| Reaction temperature | [° C.] | 90 | 90-100 |
| Stopper addition at | [NCO %] | 29.7 | 30.2 |
| Stopper addition at | [° C.] | 90 | 60 |
| After-reaction at 100° C. | [h] | 1.5 | 1.0 |
| Appearance at room temp. | [—] | clear | clear |
| NCO content | [% by mass] | 29.45 | 29.77 |
| Viscosity at 25° C. | [mPa · s] | 33 | 27 |
| Hazen color number | [—/—] | 420 | 120 |

|  | Unit | Example B1 (comparison) | Example B2 (according to the invention) |
|---|---|---|---|
| NCO content | [% by mass] | 27.31 | 28.21 |
| NCO decrease | [percentage points] | 2.14 | 1.56 |
| Viscosity at 25° C. | [mPa · s] | 73 | 62 |
| Viscosity increase | [mPa · s] | 40 | 35 |

The CD-modified isocyanate from experiment A2 has a significantly better Hazen color number at an NCO content comparable to the CD-modified isocyanate from experiment A1. After storage, the NCO content of the stored product from A2 (product from experiment B2) is significantly higher than that of the stored product from A1 (product from experiment B1).

In further experiments, modified isocyanates were prepared as described above and subjected to storage tests. The results are summarized in table 2.

TABLE 2

Storage tests (3 d, 100° C.) on modified isocyanates

| | Example: | | | | |
|---|---|---|---|---|---|
| | B11 (comp.) | B3 | B22 | B4 | B5 (comp.) |
| | | | Stopper: | | |
| | ETFMS | Phenyl-silane | Diphenyl-silane | Triphenyl-silane | Baysilon MH15 |
| | | | (Number of experiments): | | |
| | (6) av/dev$^a$ | (3) av/dev$^a$ | (2) av/dev$^a$ | (2) av/dev$^a$ | (1) |
| Hazen color number of the fresh product [—] | 372/189 | 153/13 | 150/0 | 199/32 | 200 |
| NCO decrease [percentage points] | 1.80/0.53 | 2.00/0.21 | 2.70/0.11 | 1.40/0.02 | 1.64 |
| Viscosity increase [mPa · s] | 37.0/13.1 | 39.0/7.0 | 57.0/1.0 | 29.0/2.0 | 26.0 |
| Molar ratio of catalyst:stopper | 1:13-15 | 1:15-40 | 1:15-30 | 1:15-25 | 1000$^b$ |
| Comment | c | — | d | — | e |

$^a$av = average; dev = greatest deviation from the average.
$^b$figure deviation from the other entries in *ppm of phospholine oxide based on the total mass of the reaction mixture*.
c series of experiments including experiment B1.
d series of experiments including experiment B2.
e product consisted of two phases.

These additional examples demonstrate that the addition of various silanes to carbodiimide-modified MDI effects stabilization in a similar way to the ETFMS known from the prior art, but at the same time leads to lower color numbers. Experiment B7 shows that although some stabilization can also be achieved using stoppers other than the silane stoppers according to the invention, this is associated with other disadvantages. The molar ratios of catalyst:stopper can be varied within a wide range.

II. Preparation of Prepolymers:

The two freshly prepared modified isocyanates from experiments A1 and A2 are processed to form (semi)prepolymers (prepolymers having a higher proportion by mass of monomeric isocyanate than oligomerized isocyanate for the purposes of the present invention such compounds are also subsumed under the term prepolymers) by in each case mixing the modified isocyanates with Irganox 1076, placing the mixture under nitrogen in a three-neck flask provided with reflux condenser, stirrer and gas inlet and then reacting it at 80° C. with a significant molar deficiency of the polyol according to the formulation indicated in table 2.

After a reaction time of 2.0 hours, the polyol is reacted completely and the reaction mixture is cooled to room temperature (C experiments). On these prepolymers, too, comparative tests for assessing the storage stability thereof are carried out as described above (D experiments), and the results of these tests are likewise reported in table 3.

TABLE 3

Preparation of prepolymers from the CD-modified isocyanates and storage tests

|  | Unit | Example C1 (comparison) | Example C2 (according to the invention) |
| --- | --- | --- | --- |
| Product from example A1 | [% by mass]$^a$ | 92.32 | 0 |
| Product from example A2 | [% by mass]$^a$ | 0 | 92.32 |
| Irganox 1076 | [% by mass]$^a$ | 0.18 | 0.18 |
| Polyol | [% by mass]$^a$ | 7.5 | 7.5 |
| NCO content | [%] | 24.09 | 24.45 |
| Viscosity at 25° C. | [mPa · s] | 341 | 270 |
| Hazen color number | [—/—] | 480 | 150 |

|  | Unit | Example D1 (comparison) | Example D2 (according to the invention) |
| --- | --- | --- | --- |
| NCO content | [%] | 23.58 | 24.04 |
| NCO decrease | [percentage points] | 0.51 | 0.41 |

$^a$based on the total mass of the reaction mixture.

The prepolymer from experiment D1 has, at otherwise the same composition of the reaction mixture and the same reaction conditions, a higher NCO content, a lower viscosity and a significantly lower Hazen color number than the prepolymer from experiment C1. These trends are confirmed on storage.

The invention claimed is:

1. A process for preparing organic isocyanates having carbodiimide and/or uretonimine groups or prepolymers derived therefrom, comprising:
    step (i): partially carbodiimidizating a starting isocyanate comprising an organic isocyanate or a mixture of a plurality of organic isocyanates using a catalyst of the formula cyclo-$C_4H_6P(O)R$, where R is a saturated or unsaturated, optionally substituted, organic radical, and subsequently
    step (ii): carbodiimidization reactions at a temperature of ≤80° C. by addition of a stopper comprising,
    an organic silane of the general formula $H_nSiX_{4-n}$, where n is a natural number in the range from 1 to 3 and X is a saturated or unsaturated, optionally substituted, organic radical.

2. The process of claim 1, wherein an isocyanate having an APHA Hazen color number of ≤100 is used as starting isocyanate.

3. The process claim 1, wherein the starting isocyanate is selected from the group consisting of
    tolylene diisocyanate (TDI) and
    methylenedi(phenyl isocyanate) as isomer mixture in any proportions of the 2,2', 2,4' and 4,4' isomers.

4. The process of claim 1, wherein the starting isocyanate is selected from the group consisting of
    4,4'-methylenedi(phenyl isocyanate) containing up to 4.0% by mass of 2,2'-methylenedi(phenyl isocyanate), based on the total mass of all methylenedi(phenyl isocyanate) isomers, and
    a mixture, of 2,4'-methylenedi(phenyl isocyanate) and 4,4'-methylenedi(phenyl isocyanate) containing up to 4.0% by mass of 2,2'-methylenedi(phenyl isocyanate), based on the total mass of all methylenedi(phenyl isocyanate) isomers.

5. The process of claim 1, wherein the starting isocyanate contains at least 99.0% by mass, based on the total mass of the starting isocyanate, of methylenedi(phenyl isocyanate) isomers, where the proportion of 4,4'-methylenedi(phenyl isocyanate), based on the totality of all methylenedi(phenyl isocyanate) isomers in the starting isocyanate, is at least 97.0%.

6. The process of claim 1, wherein the starting isocyanate is a mixture of methylenedi(phenyl isocyanate) isomers and polymethylenepolyphenylene polyisocyanate having a total content of methylenedi(phenyl isocyanate) isomers of from 15% by mass to <95% by mass, based on the total mass of methylenedi(phenyl isocyanate) isomers and polymethylenepolyphenylene polyisocyanate.

7. The process of claim 1, wherein:
    X=phenyl and n=2 or 3.

8. The process of claim 1, wherein the catalyst one of the following compounds or a mixture of the two:

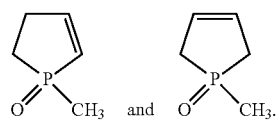

9. The process of claim 1, wherein the carbodiimidization reaction in step (i) is carried out in the temperature range from 50° C. to 150° C.

10. The process of claim 1, wherein the carbodiimidization reaction of step (i) is stopped according to step (ii) on reaching a degree of carbodiimidization in the range from 3.0% to 50%.

11. The process of claim 1, wherein a molar ratio organic silane to catalyst in the range from 1 to 20 is used.

12. The process of claim 1, wherein the reaction mixture of step (i) is cooled to a temperature in the range from 50° C. to 70° C. before carrying out step (ii).

13. The process of claim 1, wherein no further stopper in addition to the silane is used in step (ii).

14. The process of claim 1, wherein a further stopper selected from the group consisting of acids, acid chlorides, sulfonic esters and mixtures of the abovementioned substances is used in addition to the silane in step (ii).

15. The process of claim 1, further comprising reacting the organic isocyanate having carbodiimide and/or uretonimine groups obtained in step (ii) with a polyol to give a prepolymer.

* * * * *